United States Patent [19]
Fleche et al.

[11] Patent Number: 4,543,168
[45] Date of Patent: Sep. 24, 1985

[54] PROCESS FOR THE PREPARATION OF KETONES CORRESPONDING TO 1,4-3,6-DIANHYDROHEXITOLS BY ANODIC ELECTROOXIDATION

[75] Inventors: Guy Fleche, Merville; Antoine Gaset; Jacquet Fabienne, both of Toulouse, all of France

[73] Assignee: Roquette Freres, Lestrem, France

[21] Appl. No.: 606,233

[22] Filed: May 2, 1984

[30] Foreign Application Priority Data

May 4, 1983 [FR] France ................. 83 07458

[51] Int. Cl.$^4$ ............................................. C25B 3/02
[52] U.S. Cl. ................................................. 204/78
[58] Field of Search ................................. 204/78, 72

[56] References Cited

U.S. PATENT DOCUMENTS 4,097,346  6/1978  Robertson .................. 204/78
4,297,181 10/1981  Shono ........................ 204/78

Primary Examiner—R. L. Andrews
Attorney, Agent, or Firm—Larson and Taylor

[57] ABSTRACT

Process for the preparation of ketone derivatives of isomannide and of isosorbide, wherein an aqueous solution of isomannide or of isosorbide comprising an electrolyte, particularly an alkali halide, preferably a bromide and, more preferably still, sodium bromide, are subjected to anodic electrooxidation.

12 Claims, No Drawings

PROCESS FOR THE PREPARATION OF KETONES CORRESPONDING TO 1,4-3,6-DIANHYDROHEXITOLS BY ANODIC ELECTROOXIDATION

The invention relates to a process for preparing ketones corresponding to 1,4-3,6-dianhydrohexitols.

It is recalled that the ketones concerned are derived from said 1,4-3,6-dianhydrohexitols by oxidation of only the endo hydroxyl functions; now, dianhydromannitol or isomannide comprises two endo hydroxyl functions and dianhydrosorbitol or isosorbide includes one of them.

Isomannide and isosorbide are obtained from the corresponding hexitols by removing two molecules of water per hexitol; this water removal can be carried out in the presence, for example, of strong inorganic acids or of strongly acid ion exchange resins.

Isomannide and isosorbide have the same plane formula as follows:

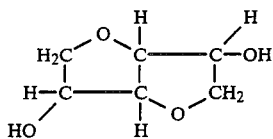

and are distinguished by the fact that:
- isomannide has its two hydroxyls in the endo position,
- isosorbide having one of its two hydroxyls (that which is connected to the carbon at the 5 position) in the endo position, the other being in the exo position.

Due to the fact that the endo hydroxyl can form a hydrogen bond with the oxygen of the ether group of the other nucleus, isomannide comprises two hydrogen bonds and isosorbide only one.

The oxidation of only one of the two endo hydroxyl groups of isomannide leads to a monoketone, 1,4-3,6-dianhydro-D-fructose, that of the two endo hydroxyl groups to a diketone, 1,4-3,6-dianhydro-D-threo-2,5-hexodiulose.

The oxidation of the single endo hydroxyl group of isosorbide leads to a monoketone, namely 1,4-3,6-dianhydro-L-sorbose.

These three compounds constitute valuable products as intermediates of synthesis.

It is already known to transform by oxidation the endo hydroxyls of dianhydrohexitols into the ketone function by the action of oxygen in the presence of a noble metal-based catalyst (particularly platinum/charcoal).

The drawback of the catalytic oxidation resides in the fact that:
- the conversion yield is moderate, not exceeding about 40% in the case of isosorbide,
- only solutions weakly concentrated in the starting dianhydrohexitol can be treated.

It is a particular object of the invention to overcome these drawbacks and to provide a process for the preparation of ketone derivatives of isomannide and of isosorbide which responds better than those preexisting to the various exigencies of practice.

Now, Applicants have found that this objective could be attained by subjecting isomannide and isosorbide to anodic electrooxidation.

It follows that, in accordance with the invention, the process for the preparation of ketone derivatives of isomannide and of isosorbide comprises subjecting to anodic electrooxidation an aqueous isomannide or isosorbide solution containing an electrolyte, particularly an alkali halide and preferably a bromide.

In an advantageous embodiment of the process according to the invention, the said aqueous solution comprises particularly NaBr at a concentration from 0.5 to 11% by weight, preferably from 1 to 5% by weight, and isomannide or isosorbide at a concentration from 0.5 to 40%, preferably from 15 to 25% by weight, the pH of said solution being from 5 to 10, preferably from 6 to 8, and the electrooxidation being effected at a temperature from 10° to 60° C., preferably from 15° to 20° C., with electricity applied in an amount of from 50,000 to 500,000, preferably from 300,000 to 500,000 coulombs per mole of isomannide or isosorbide treated.

In another advantageous embodiment, the reaction according to the invention is carried out in an electrolytic cell comprising electrodes preferably comprising platinum or carbon, the anodic and cathodic compartments being possibly separated by a diaphragm.

Other features of the invention will appear in the following description which refers to advantageous embodiments.

Consequently, in order to oxidize into the ketone function the endo hydroxyl groups of isomannide and isosorbide, procedure is as follows or an equivalent manner.

Aqueous solution of isomannide and isosorbide of concentration of 0.5 to 40% by weight, preferably from 15 to 25% by weight, are prepared by dissolving dianhydrohexitol in suitable amount in water.

To the solution thus formed, an electrolyte is added which is advantageously constituted by an alkali halide; preferably, recourse is had to a bromide, particularly NaBr which is dissolved in an amount such that the concentration of the solution in bromide is brought to 0.5 to 11%, preferably from 1 to 5% by weight.

The pH of the solution is adjusted to a value of 5 to 10, preferably from 6 to 8, more preferably to 7.

The solution thus prepared is introduced into the tank of an electrolysis cell comprising electrodes, preferably of platinum or of carbon, its temperature is brought to a value preferably close to ambiant temperature, particularly from 15° to 20° C., and between the electrodes is applied a potential difference sufficient to cause the electrolyte containing the dianhydrohexitol to be traversed by an electric current, so as to apply to it a sufficient amount of electricity, selected preferably between about 400,000 and 500,000 coulombs/mole to give an optimum yield.

Experience has proved that the "exo" hydroxyl function of isosorbide was not oxidized under these conditions (this observation has been confirmed by way of of an experiment carried out on the third dianhydrohexitol of the same plane formula as the two preceding ones, i.e. dianhydroiditol; in fact, dianhydroiditol does not undergo any oxidation of its two hydroxyl functions which are both in the exo position).

In tests intended to permit the determination of the best experimental conditions and which will be considered below, there is meant by:
yield, in the case of isosorbide, the ratio $$\frac{\text{number of moles of ketone formed}}{\text{number of moles of starting dianhydrohexitol}} \times 100$$

(the fact that, in the case of isomannide, there is the formation of a mono- and of a diketone, leads to the consideration of two yields)

the faradic yield, the ratio $$\frac{\text{theoretical amount of electricity}}{\text{experimental amount of electricity}} \times 100$$

in which:
(a) the theoretical amount of electricity or Qi. th. is well known by the formula $$Qi\text{-}th. = a \times F \times n$$

with

F = 96,500 coulombs
n = number of moles of the derivative obtained
a = number of electrons brought used (b) the experimental amount of electricity or Qi-.exp., is given by the formula $$Qi\text{-}exp. = I \times t$$

with

I = intensity of the current passing through the electrodes
t = time during which the current of intensity I passes through the cell.

Among the electrolyates which can be employed, the bromides are the most advantageous, as results from a certain number of experiments consisting of the oxidation of isosorbide with other salts (concentration of isosorbide 1.46% by weight, pH 7, current density 25 A/dm$^2$, temperature 19° C. and experimental amount of electricity 300,000 coulombs per mole) and of which the results are collected in Table I.

TABLE 1

| Nature of the salt | Concentration % by weight | Yield % | Faradic yield % |
|---|---|---|---|
| NaBr | 1.03 | 57 | 37 |
|  | 3.09 | 71 | 47 |
| KBr | 1.19 | 50 | 32 |
| KI | 3.32 | 20 | 13 |
| NaCl | 2.34 | 13 | 8 |
| Na$_2$SO$_4$ | 0.7 | 0 | 0 |

In Table II, the values recorded were recorded when varying the concentration of NaBr, the other conditions being those of the preceding series of experiments.

TABLE II

| Concentration of NaBr % by weight | Yield % | Faradic Yield % |
|---|---|---|
| 1.03 | 57 | 33 |
| 3.09 | 67 | 43 |
| 5.15 | 73 | 47 |
| 10.3 | 77 | 52 |

It results from this table that beyond a concentration of 5% NaBr, the gain in yield is low.

Adjustment of the pH to the above-mentioned preferred values is determining, as results from a group of experiments for which the other variable conditions were fixed as follows:

concentration of isosorbide: 1.46% by weight
concentration of NaBr: 3.09% by weight
temperature: 19° C.
current density: 25 A/dm$^2$
experimental amount of electricity: 300,000 coulombs/mole, the pH being brought to the different values desired by the addition of NaOH.

In fact, from the results collected in Table II below

TABLE III

| pH | Yield % | Faradic yield % |
|---|---|---|
| 2 | 0 | 0 |
| 4 | 0 | 0 |
| 5 | 13 | 8.5 |
| 6 | 43 | 27 |
| 7 | 73 | 47 |
| 9 | 23 | 14 |
| 10 | 8 | 5 |
| 12 | 0 | 0 | it is observed that from pH 8 to pH 9, there is a distinct drop in yield, due to the decomposition of the monoketone.

It is observed besides, that if the pH is initially fixed at 7, it has a tendency to drop and approach 5, at which value the yield has already substantially dropped.

Supervision of the pH and its maintenance as close as possible to 7 are hence important.

Another series of experiments, intended to establish the role of the temperature of the solution, shows that in fact ambiant temperature and particularly the temperature of 19° C. is the most favorable, the parameters fixed being:

concentration of isosorbide: 1.46% by weight
concentration of NaBr: 3.09% by weight
pH: 7
current density: 25 A/dm$^2$
experimental amount of electricity: 300,000 coulombs/mole.

The results are collected in Table IV.

TABLE IV

| Temperature in °C. | Yield % | Faradic Yield % |
|---|---|---|
| 5 | 64 | 41 |
| 15 | 66 | 41 |
| 19 | 71 | 47 |
| 40 | 51 | 34 |
| 60 | 47 | 30 |

The current density applied does not constitute a very critical magnitude, as results from the following group of experiments in which the parameters fixed are:

concentration of isosorbide: 1.46% by weight
concentration of NaBr: 5.15% by weight
temperature: 19° C.
pH: 7
experimental amount of electricity: 300,000 coulombs/mole,
the current density varying from 2.5 to 45 A/dm$^2$.

The results are collected in Table V.

TABLE V

| Current density A/dm$^2$ | Yield % | Faradic Yield % |
|---|---|---|
| 2.5 | 71 | 47 |
| 7 | 70 | 45 |
| 15 | 67 | 43 |
| 25 | 71 | 47 |

TABLE V-continued

| Current density A/dm$^2$ | Yield % | Faradic Yield % |
|---|---|---|
| 45 | 73 | 48 |

The choice of an experimental amount of electricity of 400,000 to 500,000 coulombs/mole is selected by reason of the fact that below 400,000 coulombs per mole, the yield is too low and that above 500,000 coulombs per mole, the benefit of increase in yield is counter-balanced by the appearance of by-products.

There was carried out, in this respect, a series of experiments by varying the amount of electricity and by keeping the following fixed parameters:
concentration of isosorbide: 1.46% by weight
concentration of NaBr: 1.03%
temperature: 19° C.
pH: 7
current density: 25 A/dm$^2$.
The results are collected in Table VI.

TABLE VI

| Experimental amount of electricity coulombs/mole | Yield % | Faradic yield % |
|---|---|---|
| 0 | 0 | 0 |
| 14,000 | 7 | 97 |
| 50,000 | 16 | 65 |
| 100,000 | 28 | 52 |
| 200,000 | 45 | 42 |
| 300,000 | 61 | 38 |
| 400,000 | 73 | 34 |
| 500,000 | 81 | 30 |

From reading this table, it is observed that the yield of the reaction and faradic yield vary in opposite directions.

From the measurements carried out, it results, that for an amount of electricity of 450,000 coulombs/mole, there is a yield of 77% and a faradic yield of 32%, which corresponds to particularly advantageous conditions from the economic point of view.

Finally regarding the last parameter, namely the concentration of the solution in dianhydrohexitol, it was possible to select it within relatively wide range of which the upper limit corresponds to a threshold beyond which the reaction, although still possible, is disturbed by diffusion phenomena.

Within the range of concentrations indicated, the variation of the concentration of the dianhydrohexitol has not a very great influence, as results from the series of experiments carried out by varying said concentration as well as the amount of electricity for certain concentrations, the fixed parameters being:
concentration of NaBr: 1.03% by weight
temperature: 19° C.
pH: 7
current density: 25 A/dm$^2$.
The results recorded are collected in Table VII.

TABLE VII

| Concentration in % by weight | Experimental amount of electricity in coulombs/mole | Yield % | Faradic Yield % |
|---|---|---|---|
| 0.73 | 600,000 | 42* | 14 |
| 1.46 | 300,000 | 61 | 38 |
| 7.3 | 150,000 | 32 | 97 |
| 15.8 | 8,300 | 4 | 97 |
|  | 33,300 | 15 | 87 |
|  | 66,600 | 23 | 68 |
|  | 122,500 | 39 | 59 |
|  | 245,800 | 59 | 46 |
|  | 450,000 | 78 | 30 |
| 24.8 | 64,000 | 19 | 65 |
|  | 78,000 | 25 | 62 |
|  | 236,000 | 52 | 44 |

* + by-products

This being the case, some numerical examples are given below illustrating the process according to the invention.

EXAMPLE 1

Preparation of 1,4-3,6-dianhydro-L-sorbose

Recourse was had to a cell not divided into anodic and cathodic compartments and equipped with two platinum electrodes, with a saturated calomel reference electrode, with a mechanical stirrer, with a glass electrode connected to a pH meter and a thermostated jacket.

Two experiments were carried out.

The temperature being fixed at 19° C., into the above-said cell 100 cm$^3$ an aqueous solution containing, in the first experiment, 1.42 g (9.7 mmoles) of isosorbide was poured and, in the second experiment, 29.7 g (20.3 mmoles) of isosorbide, the amount of NaBr being 1.03 g (10 mmoles).

In both cases a voltage of 20 V was applied, the current density being 25 A/dm$^2$. The pH varied from 7 to 5. Each time that the amount of electricity that had passed through the cell was equal to 500,000 coulomb/mole the experiment was stopped.

After removal of the sodium bromide (separation by liquid chromatography) and evaporation of the water, in the two experiments there were collected respectively 1.09 g and 22.65 g of monoketone corresponding, in the first experiment, to a yield of monoketone of 79% and a faradic yield of 30% and, in the second experiment, to a yield of 79.5% and a faradic yield of 30%.

EXAMPLE 2

Oxidation of the endo hydroxyls of isomannide

By using the equipment of Example 1, 100 cm$^3$ of an aqueous isomannide solution of concentration 1.46% was treated.

The NaBr concentration was 5.15%.

The current density applied to the electrodes was 15 A/dm$^2$, the temperature of the solution was 19° C. and the pH 7. The experiment was stopped when 300,000 coulombs/mole had passed through the cell.

Yields of mono- and diketone were respectively 49% (0.71 g) and of 32% (0.48 g).

As is self-evident and as emerges besides already from the foregoing, the invention is in no way limited to those of its types of application and embodiments which have been more particularly envisaged; it encompasses, on the contrary, all modifications.

We claim:

1. Process for the preparation of ketone derivatives of isomannide and of isosorbide which comprises subjecting to anodic electrooxidation an aqueous isomannide or isosorbide solution containing an electrolyte.

2. Process according to claim 1, wherein the aqueous isomannide or isosorbide solution contains an alkali halide.

3. Process according to claim 1, wherein the aqueous isomannide or isosorbide solution contains an alkali bromide.

4. Process according to claim 1, wherein the aqueous isomannide or isosorbide solution contains sodium bromide.

5. Process according to claim 1, wherein said aqueous solution comprises NaBr at a concentration from 0.5 to 11% by weight, isomannide or isosorbide at a concentration from 0.5 to 40%, the pH of said solution being from 5 to 10, wherein electrooxidation is effected at a temperature from 10° to 60° C. with electricity applied in an amount of from 50,000 to 500,000 coulombs per mole of isomannide or isosorbide treated.

6. Process according to claim 1, wherein said aqueous solution comprises NaBr at a concentration from 1 to 5% by weight.

7. Process according to claim 1, wherein said aqueous solution comprises isomannide or isosorbide at a concentration from 15 to 25% by weight.

8. Process according to claim 1, wherein said aqueous solution has a pH from 6 to 8.

9. Process according to claim 1, wherein said electrooxidation is effected at a temperature from 15° to 20° C.

10. Process according to claim 4, wherein the electricity applied during electrooxidation is from 300,000 to 500,000 coulombs per mole of isomannide or isosorbide treated.

11. Process according to claim 1, wherein the reaction is employed in an electrolytic cell comprising electrodes comprising platinum or carbon.

12. Process according to claim 1, wherein the reaction is employed in an electrolytic cell, the anode and cathode compartments being separated by a diaphragm.

* * * * *